(12) United States Patent
Yu (10) Patent No.: US 10,589,116 B1
(45) Date of Patent: Mar. 17, 2020

(54) WEARABLE PAIN MANAGEMENT APPARATUS AND METHOD

(71) Applicant: Simon Siu-Chi Yu, Oakland, CA (US)

(72) Inventor: Simon Siu-Chi Yu, Oakland, CA (US)

(*) Notice: Subject to any disclaimer, the term of this patent is extended or adjusted under 35 U.S.C. 154(b) by 0 days.

(21) Appl. No.: 16/508,131

(22) Filed: Jul. 10, 2019

Related U.S. Application Data (60) Provisional application No. 62/766,535, filed on Oct. 23, 2018.

(51) Int. Cl.
| | |
|---|---|
| *A61N 1/00* | (2006.01) |
| *A61N 2/00* | (2006.01) |
| *A61N 2/02* | (2006.01) |
| *A61H 23/02* | (2006.01) |
| *A61N 5/06* | (2006.01) |

(52) U.S. Cl.
CPC ......... *A61N 2/002* (2013.01); *A61H 23/0218* (2013.01); *A61N 2/008* (2013.01); *A61N 2/02* (2013.01); *A61N 5/0625* (2013.01); *A61H 2201/10* (2013.01); *A61H 2201/165* (2013.01); *A61H 2201/1626* (2013.01); *A61H 2201/1661* (2013.01); *A61H 2201/5097* (2013.01); *A61H 2205/062* (2013.01); *A61H 2205/081* (2013.01); *A61N 2005/0645* (2013.01); *A61N 2005/0652* (2013.01); *A61N 2005/0659* (2013.01)

(58) Field of Classification Search
CPC .......... A61N 2/002; A61N 2/008; A61N 2/02; A61H 23/00; A61H 23/02; A61H 23/0218
USPC ..................................................... 600/14–15
See application file for complete search history.

(56) References Cited

U.S. PATENT DOCUMENTS

| 4,732,140 A * | 3/1988 | Stoffregen | ............. A61H 23/00 |
| | | | 601/46 |
| 2018/0078449 A1* | 3/2018 | Callow | .............. A61H 23/0263 |

* cited by examiner

*Primary Examiner* — John P Lacyk
(74) *Attorney, Agent, or Firm* — Lyman Moultan, Esq.; Moulton Patents PLLC (57) ABSTRACT

A wearable pain management apparatus includes a drum shaped oscillatory motion driver mounted with electromagnetic coils attached to a non-stretching belt tightly strapped around a user's waist. The driver's top surface is pressed against the back of the user's waist. A belt has a ratchet buckle and a group of elongated tracks. A holster with a battery pack is securely clipped onto the belt. A center mounted motor drives a set of torque conversion planetary gears. An off center mounted mass rotates and causes unbalance and an oscillatory motion. A power cable laminated between two surfaces of the belt body terminates on a switch. The user holds a deep breath while pulling hard on the belt end causing the ratchet buckle to lock on the tracks. This action effectively places hand pressure on the apparatus rubbing on their back via the Oscillatory Pulsed Electromagnetic Field to speedily alleviate pain.

19 Claims, 9 Drawing Sheets

WEARABLE PAIN MANAGEMENT APPARATUS AND METHOD

CROSS-REFERENCE TO RELATED APPLICATION

This application claims the benefit of the priority date of earlier filed U.S. Provisional Patent Application Ser. No. 62/766,535, titled 'Wearable Pain Management Apparatus and Method,' filed Oct. 23, 2018 by Simon Yu incorporated herein by reference in its entirety.

BACKGROUND OF THE INVENTION

An estimated 70 percent of all human adults experience some form of back pain during their lifetime. Back pain can be attributed to a number of factors, including physical activity, obesity, injury, poor posture, stress and even the simplest of movements like picking something up incorrectly or with no apparent reason. Particularly, lower back pain is also one of the leading causes of job disability in the world. With the advanced technologies of today, treatments include over-the-counter pain relievers, massage, muscle relaxants, topical pain relievers, narcotics, injections medications, and the final resort to surgery.

Massaging is one of the best alternatives to alleviate back pain and merely requires a good massage therapist in the person's local area. But due to things like busy schedules, travel times and personal privacy, getting a hands-on massage may not work for every person's lifestyle. A better substitute for human touch is needed to help those who suffer back pain.

There has therefore been a long unsatisfied demand in the market for a pain management apparatus and method for physical therapy without the disadvantages mentioned above.

SUMMARY OF THE INVENTION

An embodiment of the invention is a standalone, hands free device which does not require an assistant when performing pain relief massage action and yet mimics the physical feel and pressure as if applies from a massage therapist. An advantage of the invention is self-performing pain relief at the comfort and total privacy of one's home. Another advantage of the invention is user performing pain relief at many orientations including laying face down, while walking, while running, doing exercise, yoga, etc.

In another embodiment, the invention is portable and can be carried when travelling. Other advantages of the invention include the device being placed on any position along the spinal column to be massaged. The device can also be used for massage leg, thigh, and calf. Once the tracked belt is locked with the ratchet buckle, it creates a great amount of back pressure, causing the oscillatory motion driver to tightly press against the back of the user to achieve a sensation similar to a human hands-on sensation.

In yet another embodiment, drum shaped drivers comprise a spine channel configured to allow a section of the spine to recess into the channel and avoid excessive pressure against the spine. Another advantage of the invention is the oscillatory motion driver having center mounted motor and torque conversion planetary gears. The planetary gears couple with an off center rotating mass to generate a great amount of massage force action. The alternative oscillatory motion driver and its off center mounted motor and motor case rotating generates further forces for massage action.

The drum shaped driver is configured with resultant vector pulling forces via a belt to achieve maximum back pressure applied on a user's back during massage. The driver back pressure is configured to increase with the breathing rhythm when a user inhales and decreases when the user exhales. The increased back pressure lowers sensitivity of pains receptors in the user's body. A top mounted infrared LED provides heat for relaxing deep tissues to mask pain felt by the user of the disclosed apparatus, device and system.

A pulsed Electromagnetic Field (PEMF) unit generates Oscillatory Pulsed Electromagnetic Field (OPEMF) to speed up a user's recovery from pain. The oscillatory motion driver operates at a low frequency and at a high amplitude of approximately 300 to 1200 RPM to maximize masking the pain.

Other aspects and advantages of embodiments of the disclosure will become apparent from the following detailed description, taken in conjunction with the accompanying drawings, illustrated by way of example of the principles of the disclosure.

Throughout the description, same reference numbers may be used to identify same or similar elements depicted in multiple embodiments. Although specific embodiments of the invention have been described and illustrated, the invention is not to be limited to the specific forms or arrangements of parts so described and illustrated. The scope of the invention is to be defined by the claims appended hereto and their equivalents.

DETAILED DESCRIPTION

Reference will now be made to exemplary embodiments illustrated in the drawings and specific language will be used herein to describe the same. It will nevertheless be understood that no limitation of the scope of the disclosure is thereby intended. Alterations and further modifications of the inventive features illustrated herein and additional applications of the principles of the inventions as illustrated herein, which would occur to one skilled in the relevant art and having possession of this disclosure, are to be considered within the scope of the invention.

Dimensions detailed herein and in the drawings are intended to be a guide to nominal manufacturing dimensions. The detailed dimensions may vary by plus or minus ten percent taking into account manufacturing restraints and materials for various embodiments as recited, taught and suggested herein. The dimensions therefore are applicable to at least one embodiment but are not meant to be limiting to other embodiments of the disclosure.

The present disclosure is directed to using a non-stretching belt comprising a ratchet buckle and group of elongated tracks combined with an Electromagnetic coil mounted on a high momentum drum shaped electric powered oscillatory motion driver (Oscillatory Pulsed Electromagnetic Drum OPED) that mimics human hands applying great pressure rubbing on the back of a human body with Oscillatory Pulsed Electromagnetic Field to speedily alleviate back pains. The terms "driver" and "drum" are therefore used interchangeably in the present disclosure.

Figure 1:
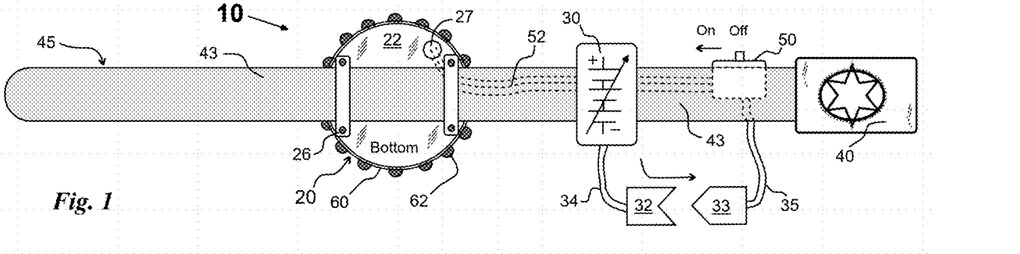
FIG. 1 is a depiction of the pain management system showing an outer side of the belt and a bottom view of the oscillatory motion driver drum in accordance with an embodiment of the present disclosure.

FIG. 1 is the wearable pain management system 10 comprising a belt body 45, outer belt 43 and inner belt 46. One end (first end) of belt body 45 terminates with a ratchet buckle 40 and other end (second) of belt body 45 laid with a group of elongated locking tracks 47 on the inner side of belt 46 in accordance with an embodiment of the present disclosure.

The system 10 further comprises a drum shaped oscillatory motion driver (Drum) 20 attached on its bottom side 22 to the inner side 46 of belt body 45 by the mounting bracket 26. The driver (Drum) 20 further comprises a bonnet 60 covering with a plurality of soft rubber nubs 62. Battery pack 30 is encased in a battery holster 31 with clip 36 securely clipped on the outer side 43 of belt body 45. The battery cable 34 connects to power output socket 32 mated to power plug 33 via cable 35. The power on/off switch 50 controls the electric current to power the motor 82 which generates strong oscillatory motion indicated with force directional arrow 87. One end of power cable 52 connects to power switch 50 and a length of cable 52 laminated between inner belt 46 and outer belt 43. A pre-determined belt length enters into access hole 27 then terminates to the CPU 92, and other components, such as Infrared LED driver 93, Pulsed Electromagnetic Field driver 91, Wi-Fi 90, motor speed control circuitry shown in FIG. 5.

Figure 1A:
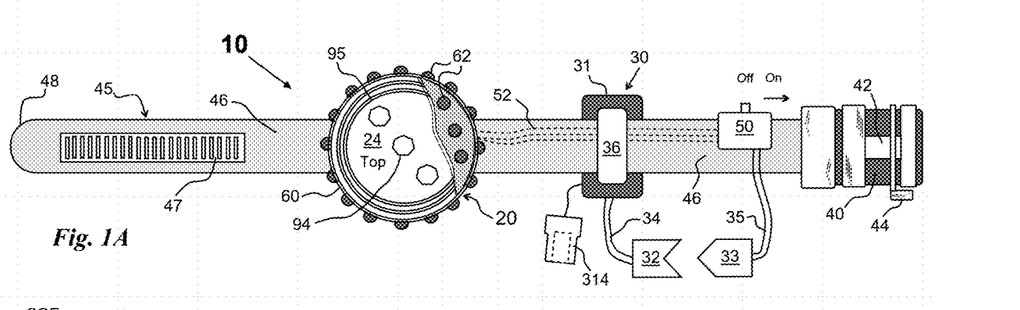
FIG. 1A is a depiction of the pain management system showing an inner side of the belt and a top view of the oscillatory motion driver drum in accordance with an embodiment of the present disclosure.

Turning to FIG. 1A is a reverse side of the system 10 showing a group of elongated tracks 47 securely stitched onto the inner side of belt 46 in accordance with an embodiment of the present disclosure. A battery hostler 31 clips onto the belt body 45. A locking blade 42 hinge is installed behind the ratchet buckle 40 and by a depressive release of button 44 will separate the buckle 40 from the tracks 47. With partial removal of bonnet 60, the top surface 24 of oscillatory motion driver 20 reveals a cluster of infrared LED 94 and a ring of Pulsed Electromagnetic coil 95, The LED 94 emits between 700 nm to 1 mm wave length infrared to pass through clothing and penetrate deep under the user's skin providing warmth to relax tight muscles. The LED 94 turns on and simultaneously enhances the effectiveness of suppressing pain with oscillatory motion driver 20 physically moving the lymphatic fluid in motion. The Pulsed Electromagnetic Field driver 91 generates high energy square wave pulses onto Electromagnetic Field coil 95.

The resulting Oscillatory Electromagnet fluxes 199 improves intercellular fluid & blood flow, stimulates electron transport in cells, and stimulates release of endorphins to mask body pains. Pulsed Electromagnetic Field 99 (PEMF) therapy had been used for decades to heal bone loss demonstrated by NASA. The present invention improves the traditional stationary Pulsed Electromagnetic Field 99 (PEMF) into Oscillatory Pulsed Electromagnetic Field 199 (OPEMF) therapy and is therefore a great advancement.

Figure 2:
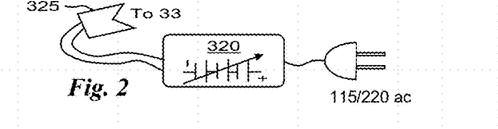
FIG. 2 is a depiction of an AC adapter converting AC to variable DC to power the pain management system without the use of battery pack at home in accordance with an embodiment of the present disclosure.
Figure 3:
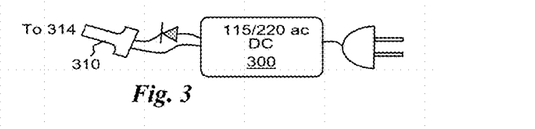
FIG. 3 is a depiction of a battery charger to recharge the battery pack in accordance with an embodiment of the present disclosure.

FIG. 2 is an AC adapter 320 converting A.C. (alternating current) to variable D.C. (direct current) via the adapter socket 325 mated to power plug 33 in order to power the system 10 at home without the use on battery pack 30. Recharging the depleted battery pack 30 is simply done via the charger plug 310 shown in FIG. 3 to battery charging socket 314. Note that the battery charger 300 is not capable of running the system 10.

Figures 4, 6:
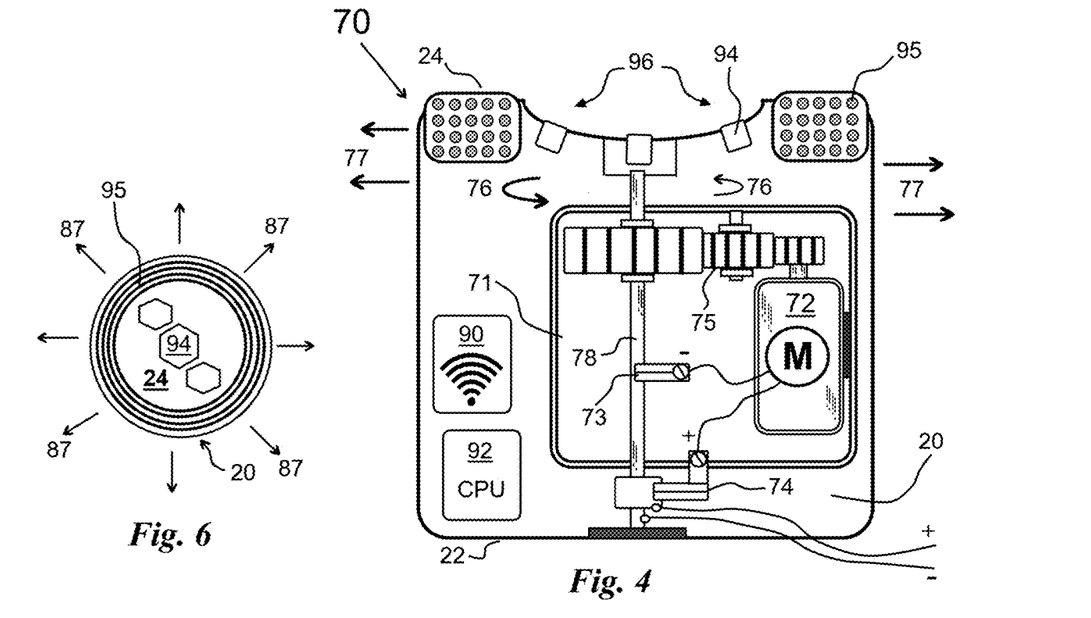
FIG. 4 is a cross section view of an alternative construction of the oscillatory motion driver comprising off-axis mounted motor and motor case to generate strong oscillatory motion in accordance with an embodiment of the present disclosure.
FIG. 6 is a top view removing a soft rubber bonnet from the oscillatory motion drum revealing infrared LED and a Pulsed Electromagnetic Field coil module in accordance with an embodiment of the present disclosure.

There are two versions of structural design 70 and 80 for the oscillatory motion driver 20. The design 70 shown in FIG. 4 depicts the rotating motor case 71 with a motor 72 coupled to a set of torque conversion gears 75 encased in a motor case 71 rotating in direction of arrow 76 as shown. The case 71 rotates out of its center axis shaft 78 to generate strong oscillatory forces indicated by directional arrow 77. Because the motor 72 and case 71 rotate around the central shaft 78, a pair of wipers 73 and 74, are needed to provide electrical power while the case 71 is spinning.

Figure 5:
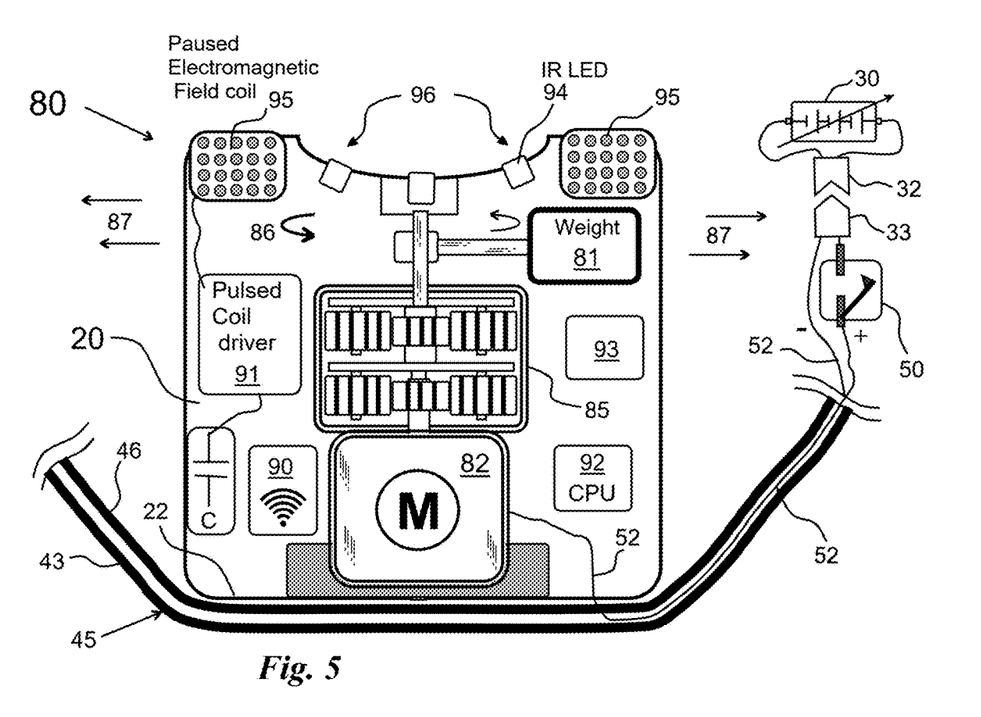
FIG. 5 is a cross section view showing construction of an oscillatory motion driver comprising a center mounted motor and planetary gears spinning an off center mass to generate strong oscillatory motion in accordance with an embodiment of the present disclosure.

Turning now to FIG. 5 is another version 80 of the oscillatory motion driver 20 in accordance with an embodiment of the present disclosure. A centrally mounted motor 82 drives a set of planetary torque conversion gears 85 which further drive an unbalanced mass 81 rotating around its center of gravity as shown by directional arrow 86 generates strong oscillatory motion force indicated in directional arrow 87.

Inside the drum 20 is a wireless transceiver unit 90 that communicates the commands from an external device such as a smart phone to control the motor 82 speed, reversing the rotation direction of motor 82 operation, timer for length of operation and instructions to the CPU 92 regarding the operation mode of infrared LED 94 and (PEMF) driver 91.

A power cable 52 shown in FIG. 5 depicts the cable 52 laminated between inner belt 46 and outer belt 43 of the belt body 45. A spine channel 96 is provided for space to allow spine 14 recessed into the concave cavity and avoid excessive pressure on the spine 14 particularly to benefit skinny and bonny users 400.

FIG. 6 is a top 24 view of an oscillatory motion driver 20 with its bonnet 60 removed in accordance with an embodiment of the present disclosure. Oscillatory motion forces are indicated with directional arrows 87.

Figure 7:
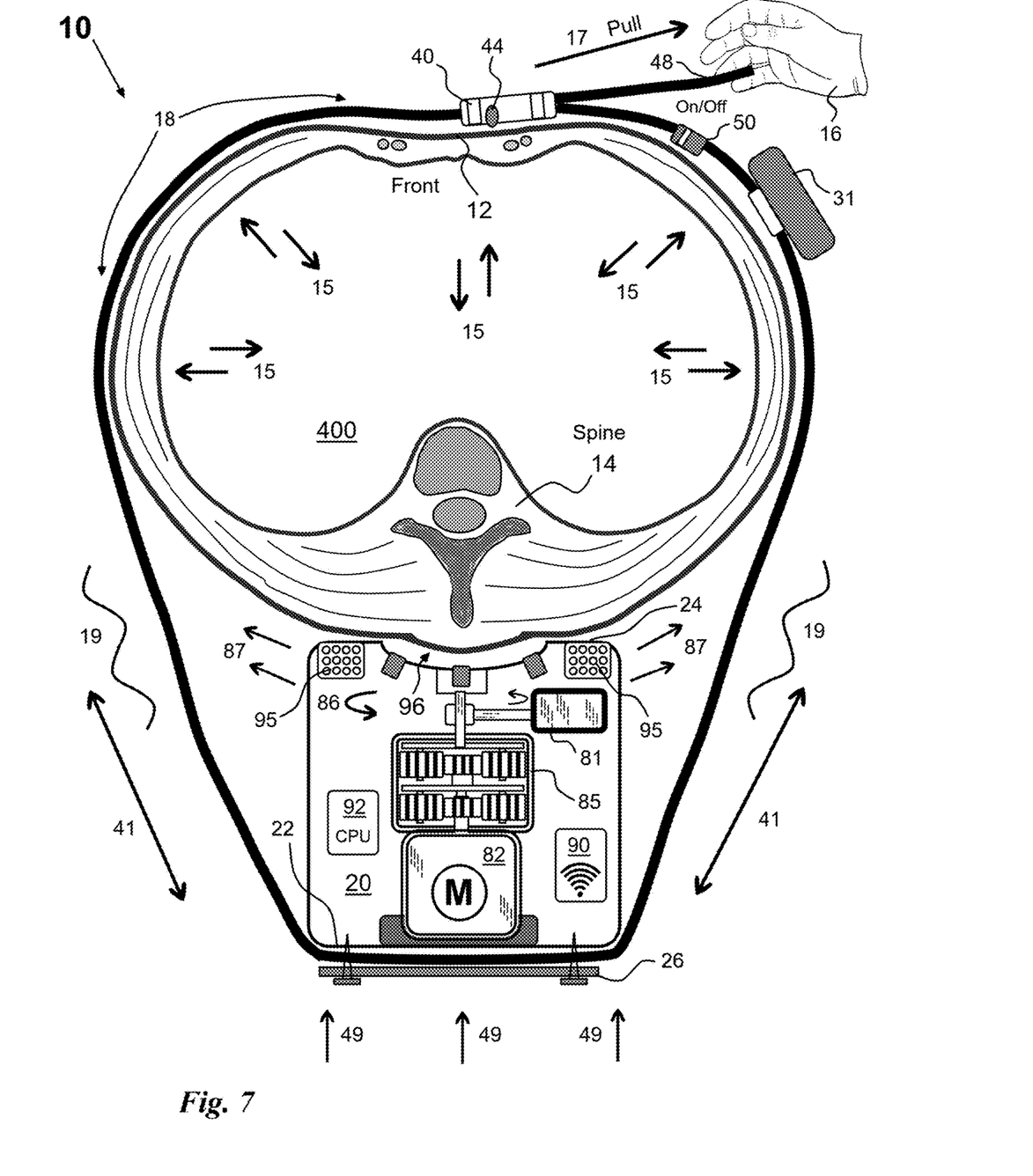
FIG. 7 is a cross section top view of a lower torso of a human body showing the pain management system strapped on the waist on abdominal area in accordance with an embodiment of the present disclosure.

Turning to FIG. 7, system 10 is depicted with a second version 80 of the oscillatory motion driver 20 from a top cross sectional view of a human 400 lower torso at the waist section in accordance with an embodiment of the present disclosure. The belt 45 is tightly strapped around a body 400. The most effective way to alleviate pain is by massage using human hands plus the therapist body weight as if leans against the user 400 back.

To affect high back pressure using the invention 10, user 400 takes a deep breath, then contracts his abdomen while quickly and tightly pulling the belt end 48 as shown by pull arrow 17 before exhaling. At this moment, the belt 45 pulls at a resulting vector force as shown by tension arrow 41. The back pressure 49 becomes so great that a human finger cannot be inserted into the interface between the top 24 of oscillatory motion driver 20 (Drum) and the user's 400 back.

When the driver (drum) 20 is energized, top 24 rubs against the back muscles in the direction shown by arrow 87. Since the user 400 naturally breathes in and out, the back pressure 49 will change to slightly lower pressure when exhaling due to contraction of the user's abdominal muscles. However back pressure 49 will greatly increase when user 400 inhales or bends his body in any direction. The abdominal muscles thus behave like a balloon changing its volume as shown by arrow 15.

FIG. 7 also illustrates how the belt 45 anchors on front of body 400 in area 18 and is not allowed to stretch, forcing the drum 20 to press the back of user 400 even harder. The fluctuation of pressure peaks and valleys create harmonic standing waves 19 as can be observed by the wave pattern along the length 41 depicted. The user 400 experiences a light to heavy sensation as a pressure fluctuation. The frequency of wave 19 is related to the respiration rate of an adult and varies from 12 to 20 fluctuations per minute. According to some reports, the most effective massage is performing at hand strokes between 8 to 20 per minute and the human brain cannot respond to frequencies above 3600 RPM anyway. Based on these findings, the present invention operating from 300 to 1200 RPM with high torque coupled with Pulsed Electromagnetic Field helps mask back pain. Conventional electric massage devices operate at 2800 to 3600 RPM and cause itching and discomfort as mentioned above in reports.

Figure 8:
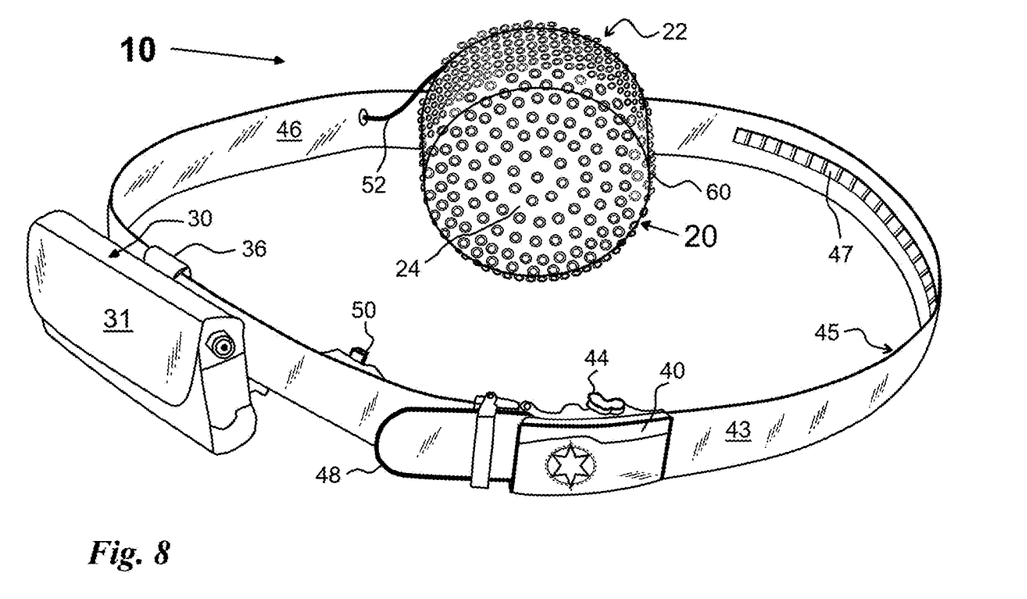
FIG. 8 is a perspective view of the pain management system showing the belt engaged with the tracks in accordance with an embodiment of the disclosure.

FIG. 8 shows system 10 with the ratchet buckle 40 engaged with the tracks 47 in accordance with an embodiment of the present disclosure. The power switch 50 is conveniently located proximal the front buckle for user 400 easy access.

Figure 8A:
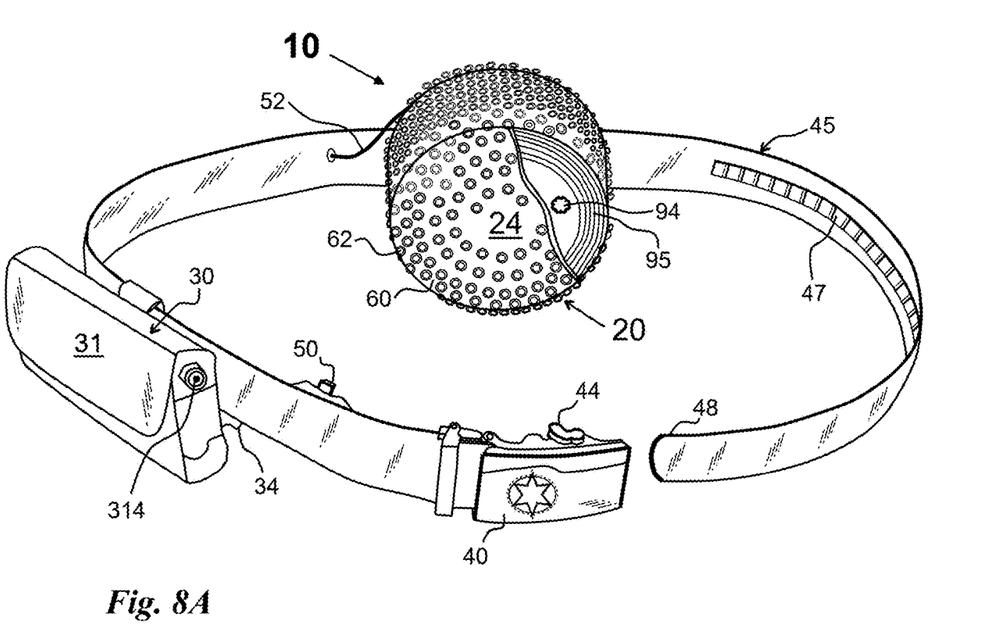
FIG. 8A is a perspective view of the pain management system showing the belt disengaged from the tracks by a press button release in accordance with an embodiment of the disclosure.

FIG. 8A shows the tracks 47 of belt 45 disengaged from ratchet buckle 40 by a depressive release via button 44 in accordance with an embodiment of the present disclosure. The battery hostler 31 can be removed if operating with A.C. power adapter 320 instead.

Figure 9:
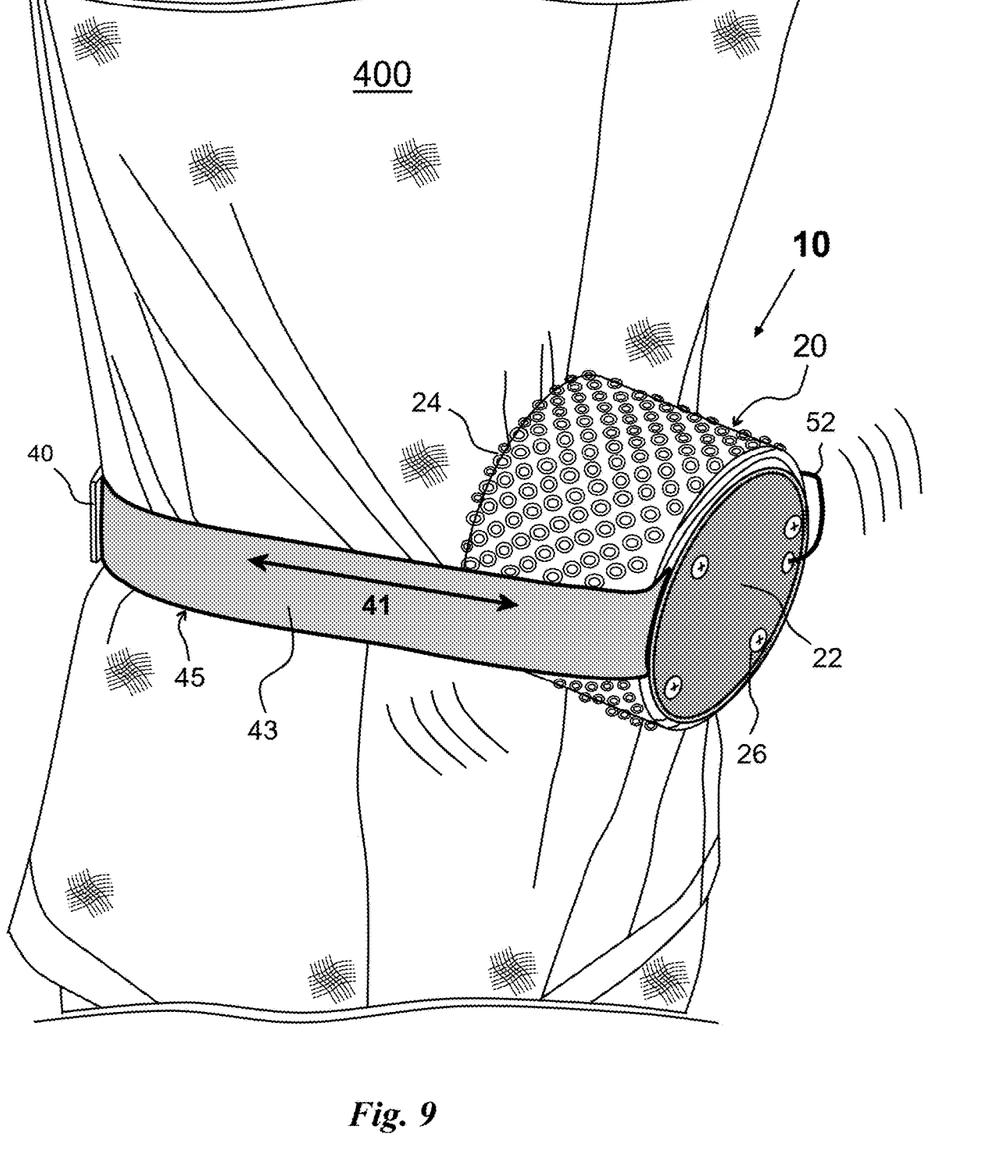
FIG. 9 is a perspective view of the pain management system being worn on the lower back of a user in accordance with an embodiment of the present disclosure.

FIG. 9 is the system 10 worn by user 400 showing drum top 24 presses against back of user 400. Length of 41 creates fluctuating harmonic standing wave 19 enhances user 400 more comfortable sensation during massage in action.

Figure 10:
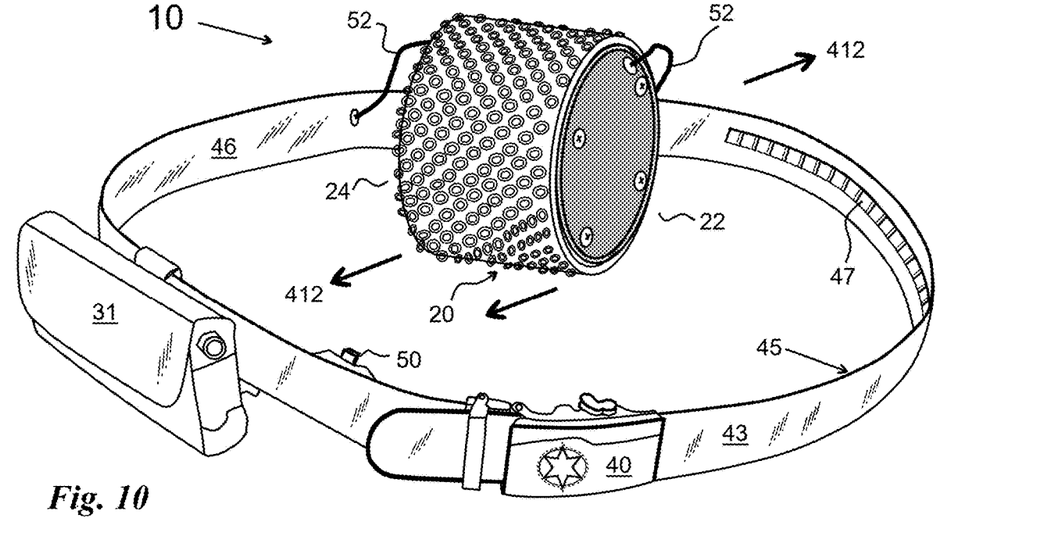
FIG. 10 is a perspective view of the pain management system repurposed for generate tapping (chopping) action to treat stiffed and tired muscles with the driver drum in the new orientation shown in accordance with an embodiment of the present disclosure.
Figure 10A:
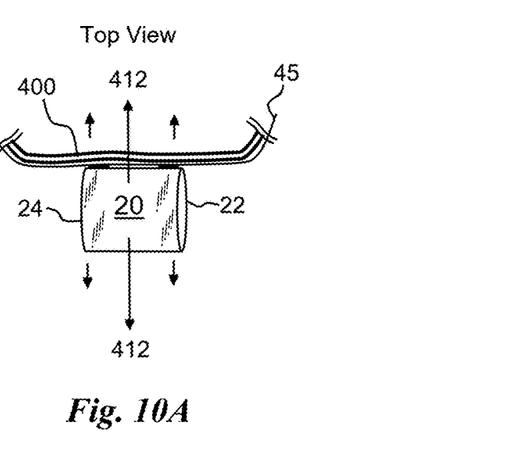
FIG. 10A illustrates a top view of the repurposed tapping action pain system being worn by a user in accordance with an embodiment of the present disclosure.

FIG. 10 is the system 10 repurposed to produce a tapping and a chopping motion indicated by directional arrow 412 in accordance with an embodiment of the present disclosure. The oscillatory motion driver 20 is re-orientated to turn 90 degrees from previous depictions. This configuration helps user 400 as shown in FIG. 10A per a top view of system 10 to loosen his stiff and tired muscles.

Figure 11:
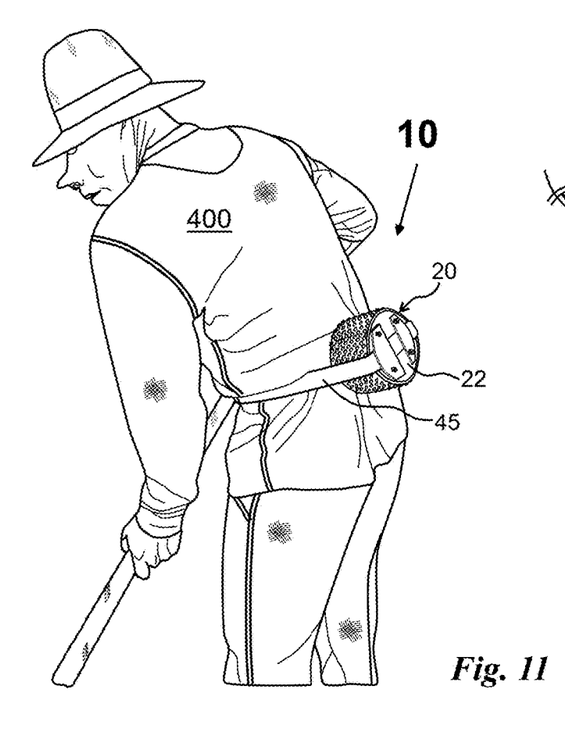
FIG. 11 is a perspective view of a person strapping the invention on his back to reduce back pain while working in accordance with an embodiment of the present disclosure.

Per FIG. 11, an embodiment 10 of the present disclosure is worn by a user 400 as he performs heavy labor work to loosen up his sore muscles and alleviates his back pain.

Figure 12:
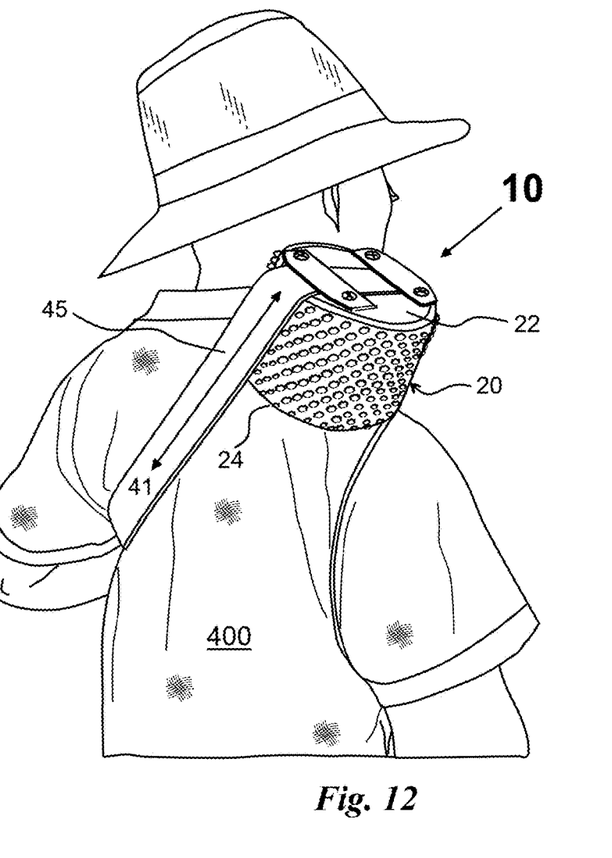
FIG. 12 illustrates strapping the invention on top of a shoulder to relieve pain in accordance with an embodiment of the present disclosure.

In FIG. 12 depicted according to an embodiment of the present disclosure, a user 400 wears the system 10 on his shoulder. Here the user can manipulate the intensity and positioning of drum 20 with his hands by pulling the belt 45 forward and backward.

Figure 13:
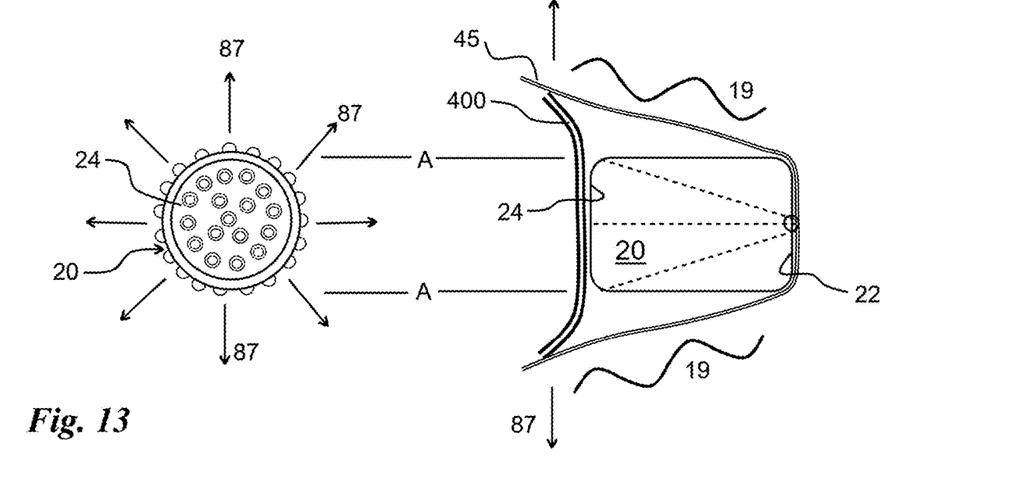
FIG. 13 is a diagram showing drum oscillation motion in a radial direction where a taller the drum results in a larger momentum in accordance with an embodiment of the present disclosure.

As illustrated in FIG. 13, a top view of driver 20 (Drum) oscillates in a radial pattern indicated by directional arrows 87 in accordance with an embodiment of the present disclosure. A taller drum 20 creates a larger momentum.

Figure 14:
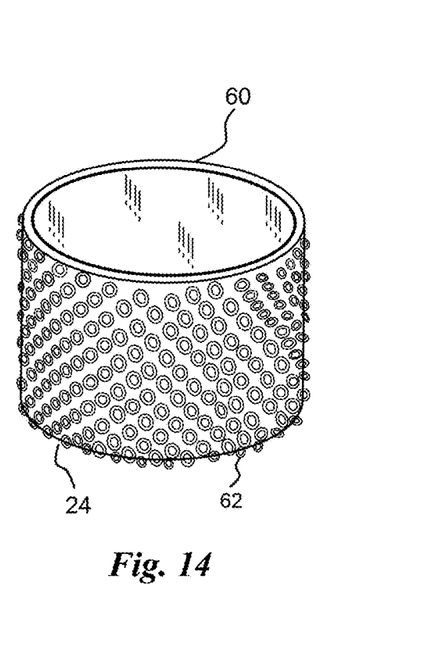
FIG. 14 is a perspective view of soft rubber bonnet to protect skinny and bonny users in accordance with an embodiment of the present disclosure.

The soft rubber bonnet 60 shown in FIG. 14 comprises soft nubs 62 covering an exterior of bonnet 60 in accordance with an embodiment of the present disclosure. The soft rubber bonnet 60 and soft nubs 62 provide a comfortable rubbing surface against the body of the user 400. The covered bonnet 60 will not block rays of the infrared LED 94 and the Electromagnetic fluxes 199 of the Electromagnetic coil 95.

Figure 15:
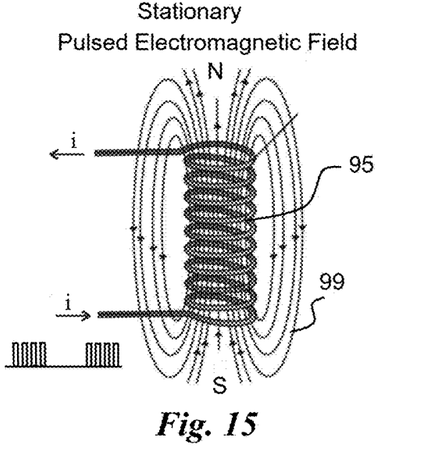
FIG. 15 is a depiction of a Stationary Magnetic flux generated from an ordinary Pulsed Electromagnetic Field (PEMF) device in accordance with an embodiment of the present disclosure.

A stationary Pulsed Electromagnetic Field 99 is generated by passing electric current through coil 95 illustrated in FIG. 15. The Pulsed Electromagnetic Field 99 can also be used by medical professional to treat patients who suffer additionally suffer from neck pain and repair cracked bone.

Figure 15A:
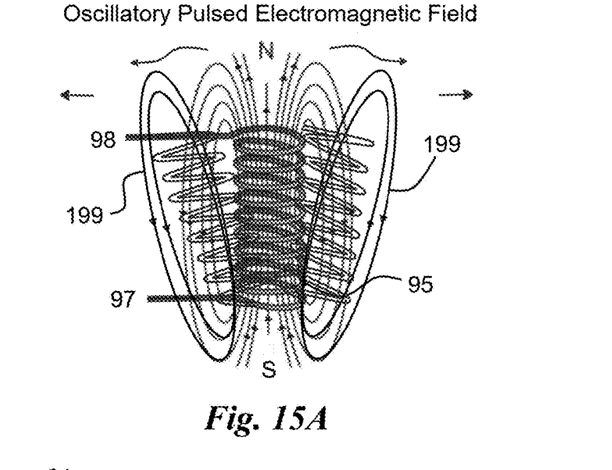
FIG. 15A is a depiction of an Oscillatory Magnetic flux generated from the present invention (OPEMF) in accordance with an embodiment of the present disclosure.
Figure 16:
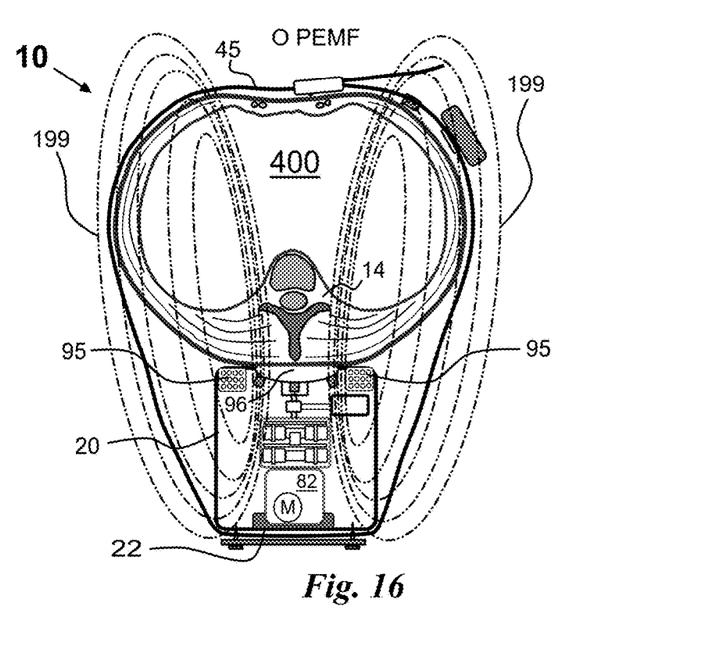
FIG. 16 is a depiction showing a user worn Pulsed Electromagnetic Filed (PEMF) generator shaking with an oscillating drum resulting in Oscillatory rubbing motion with Oscillatory Pulsed Electromagnetic Field (OPEMF) to treat back pain in accordance with an embodiment of the present disclosure.

A more advanced present invention shown in FIG. 15A is achieved by turning ordinary stationary Pulsed Electromagnetic Field 99 into Oscillatory Pulsed Electromagnetic Field 199 as shown in FIG. 16. As magnetic flux 99 passes through human tissues, the magnetic flux will also influence the cells' activity within the body in a fixed region. Because the Electromagnetic coil 95 oscillates in the same direction as the drum 20, it thus creates Oscillatory Pulsed Electromagnetic Field 199 (OPEMF) and sweeps wider areas inside the tissues to heal pains quicker.

Figure 17:
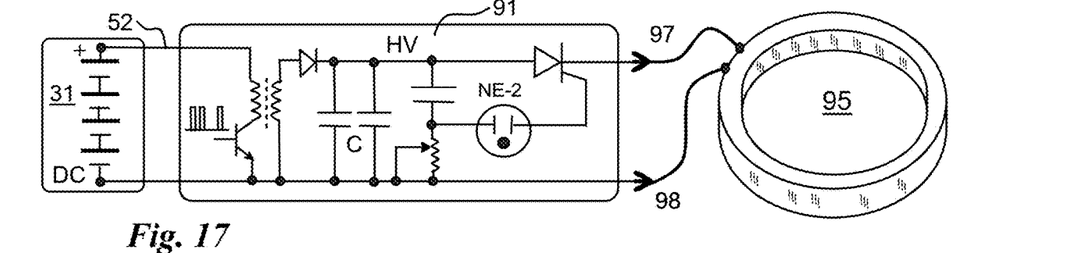
FIG. 17 is a circuit diagram showing a typical capacitor discharge circuit for powering the Pulsed Electromagnetic Field coil in accordance with an embodiment of the present disclosure.

FIG. 17 is a simplified schematic drawing of an SCR type capacitor discharge circuit to pulsed charge the Electromagnetic coil 95 in accordance with an embodiment of the present disclosure. The depicted circuit produces about 3000 Gauss of Pulsed Electromagnetic Field at 0.5 hertz to 50 Hertz. High voltage is preferable since energy stored in a capacitor is ½ CV square. Therefore, E=½ $CV^2$ in an SCR semiconductor is ideal for the purposes of the disclosure.

Figure 18:
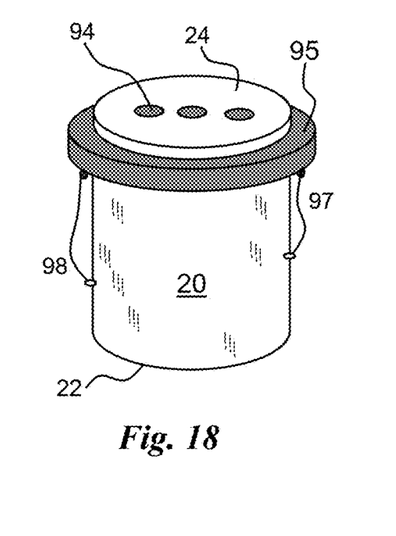
FIG. 18 is a depiction showing the Pulsed Electromagnetic Field coil module mounted on the exterior surface on the drum in accordance with an embodiment of the present disclosure.

Turning to FIG. 18 the drum 20 is depicted with bonnet 60 removed showing Electromagnetic coil 95 mounted encircling the exterior surface of drum 20. Wires 97 and 98 take power from pulsed driver 91. Coil 95 can be installed on an interior surface of drum 20 as well as shown in FIG. 16.

Figure 19:
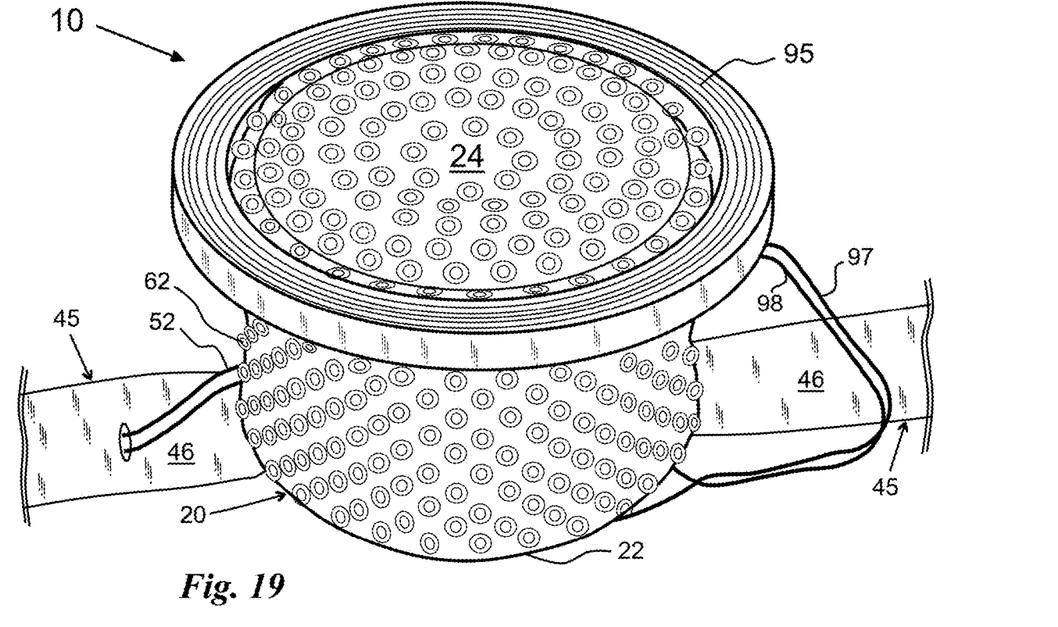
FIG. 19 is a perspective view pain management showing an electromagnetic coil module install on top side of the drum in accordance with an embodiment of the present disclosure.

FIG. 19 depicts details of a pain system 10 mounted with an electromagnetic coil module 95 on top 24 of drum 20 according to an embodiment of the present disclosure. The oscillating drum 20 carrying the coil module 95 causing the stationary pulsed electromagnetic field 99 to fluctuating in the same direction with the drum 20 which resulting the magnet fields become oscillatory pulsed electromagnetic field 199 can enhance the effectiveness of the system 10.

Figure 20:
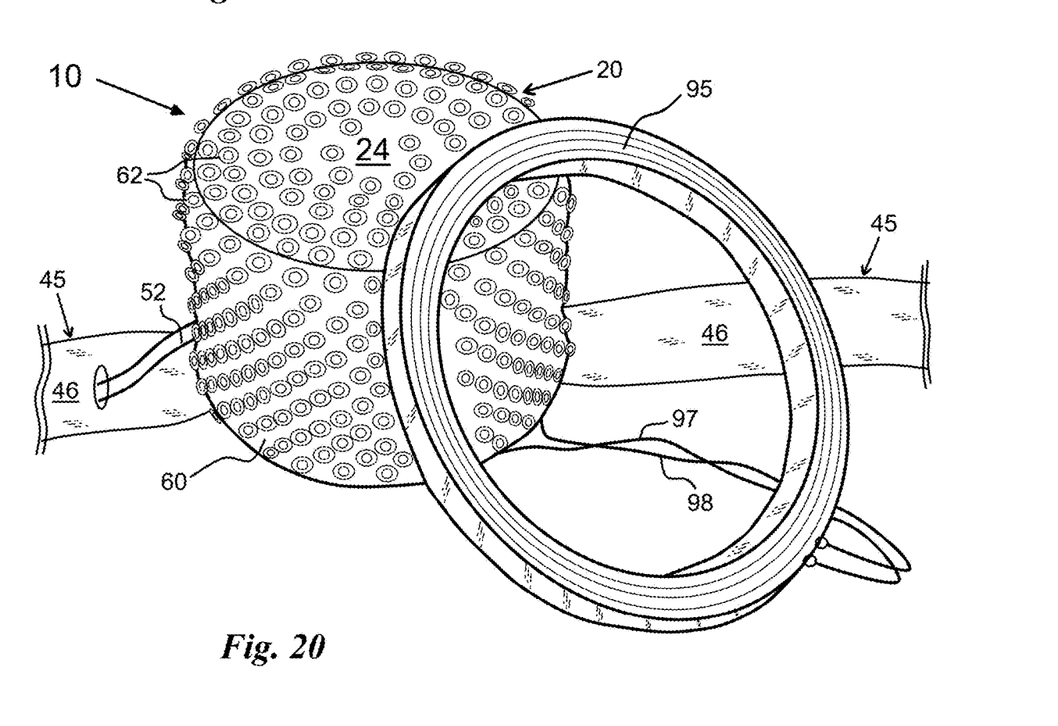
FIG. 20 is a depiction of the electromagnet coil module detached from the drum allowing users to freely operating the coil module to treat any area of their body in accordance with an embodiment of the present disclosure.

FIG. 20 shows the coil module 95 detached from the drum 20 in accordance with an embodiment of the present disclosure. The detached coil module 95 takes power from the system 10. The user can wear the system 10 on his waist while taking the coil module 95 to treat other areas.

The invention 10 enables its user 400 to perform self-massage to alleviate pain at home out of sight and without interference by the casual bystander. The system 10 is lightweight and can be stored in a drawer. One important feature is hand free operation with controllable back pressure and on-demand power level by varying supply voltage fed into the motor 82, or 72. According to Newton's second law of mechanics the numerical value of force of an object in rectilinear motion is equal to the mass of the object times its acceleration. F=MA. If the object is in rotational motion. It can be shown that this converts to F=$MV^2$/r, where V is the rotational velocity and r is the radius of rotation. In the system 10, both the unbalanced mass 81 and the off center mounted motor 72 generate centrifugal force directly proportional to the square of the rotational velocity. Rotational velocities of the motor increase with an increase in the D.C. voltage and double the rotational velocity and quadruple the force.

Another feature is the physical configuration of the belt 45 and the driver 20 (Drum). When in operation, the system 10 creates harmonic standing wave 19 due the body density and respiration frequency of individual user 400. The fluctuation of light and heavy back pressure felt is a pleasure and encourages user 400 to continue using the invention 10.

The oscillatory motion generated from drum 20, physically helps transport body fluid. The stationary Pulsed Electromagnetic Field 99 fluctuates in step with drum 20. The Oscillatory Pulsed Electromagnetic Filed 199 penetrates deeper and wider and interacts with tissues and cell activity to relieve pains fast.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

While the forgoing examples are illustrative of the principles of the present disclosure in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the disclosure be limited, except as by the specification and claims set forth herein.

What is claimed is:

1. A pain management apparatus comprising:
    an oscillatory motion driver (DSOMD) configured as a drum to generate a pressure fluctuation for relief of musculoskeletal pains;
    a Pulsed Electromagnetic Field (PEMF) coil component of the DSOMD enabled to cause PEMF to swing and spread in a plurality of directions via the oscillatory and pulsed motions of the DSOMD;
    a belt having a ratchet buckle on a first end and at least one locking track on a second end, the belt configured to receive the DSOMD; and
    a detachable battery pack comprising a power selection switch and encased in a holster with a belt clip securely fastened onto the belt.

2. The pain management apparatus of claim 1, wherein the DSOMD further comprises a motor case configured to receive an off center mounted electric motor with torque conversion gears coupled to a center shaft fixed on a base of the drum wherein the motor case spins off its geometric center and generates oscillatory motions.

3. The pain management apparatus of claim 1, wherein the DSOMD is powered by a center mounted electric motor on a base of the drum coupled to torque conversion gears spinning an off center weighted axis to generate oscillatory motions.

4. The pain management apparatus of claim 1, wherein the belt further comprises an inner side and an outer side and a power carrying cable laminated there between, the power carrying cable comprising a first end attached to one of the detachable battery pack and an external power source via a power switch and a second end terminating inside the drum.

5. The pain management apparatus of claim 1, wherein the detachable battery pack further comprises a rechargeable socket.

6. The pain management apparatus of claim 1, wherein a top surface of the drum further comprises a plurality of light emitting diodes configured to speed up healing of injured muscles with infrared energy.

7. The pain management apparatus of claim 1, further comprising a plurality of light emitting diodes installed on a surface of the drum operating in an infrared spectrum between 700 nanometers to 1 millimeter to penetrate clothing and provide blood flow increasing surface heat.

8. The pain management apparatus of claim 1, further comprising a wireless transmitter and a central processing unit in communication with a smart phone to manage motor speed, forward and reverse direction, and a PEMF intensity, a control time duration thereof and an intensity for an LED (light emitting diode).

9. The pain management apparatus of claim 1, further comprising a concave shaped channel on a top side of the drum, the concave shaped channel running perpendicular to a belt orientation to accommodate massaging a section of a user's spinal column and avoid excessive rubbing pressure on the spine.

10. The pain management apparatus of claim 1, further comprising the belt attached on a bottom side of the drum, the belt strapped tightly around a user's waist forming a closed loop and configured to vibrate with the drum and generate harmonic standing waves between a bottom edge of the drum and both sides of the waist, a frequency of the harmonic standing waves dependent on a tension of the belt.

11. The pain management apparatus of claim 1, further comprising a side wall of the drum attached onto an inner side of the belt configured inline and parallel to the belt to create a tapping and chopping motion on a back of the user.

12. The pain management apparatus of claim 1, further comprising a low durometer bonnet configured to cover the drum and low durometer nubs bonded to a surface of the bonnet for a soft rubbing and tapping impact on a user.

13. The pain management apparatus of claim 1, further comprising a PEMF Therapy System with the DSOMD, the PEMF therapy system comprising a PEMF driver and an Electromagnetic field Coil module.

14. The pain management apparatus of claim 1, further comprising an Electromagnetic Field coil module installed on an interior or on an exterior surface of the DSOMD to enable a maximum efficiency PEMF strength.

15. The pain management apparatus of claim 1, further comprising a PEMF Therapy System configured to produce a stationary PEMF when a power for the DSOMD is selectively switched off via the power selection switch to avoid treating a body area such as the face by a rubbing or by a tapping motion.

16. A method of using a wearable pain management apparatus, the method comprising:
   generating a pressure fluctuation for relief of musculo-skeletal pains via an oscillatory motion driver (DSOMD) configured as a drum;
   swinging a Pulsed Electromagnetic Field (PEMF) via oscillatory and pulsed motions of a PEMF coil component of the DSOMD,
   receiving the DSOMD via a belt having a ratchet buckle on a first end and at least one locking track on a second end;
   powering the DSOMD and the PEMF coil via a detachable battery pack comprising a power selection switch and encased in a holster with a belt clip securely fastened onto the belt; and
   strapping the belt to a user's waist with a top surface of the drum proximal a back pain area to be treated.

17. The method of claim 16, further comprising strapping the belt to a user's back and pulling the belt back and forth across a pain area of the back to effect a massage motion via the drum on the belt.

18. The method of claim 16, further comprising selectively switching power to both the DSOMD and a PEMF coil module via a power switch to affect an oscillatory rubbing motion with oscillatory pulsed electromagnetic field benefits.

19. The method of claim 16, further comprising selectively switching power off to the DSOMD via a power switch in order to avoid treating sensitive areas of the body and only using the PEMF or infrared light emitting diodes.

* * * * *